United States Patent [19]
Poulsen

[11] Patent Number: 5,300,039
[45] Date of Patent: Apr. 5, 1994

[54] SAFETY HYPODERMIC NEEDLE

[76] Inventor: Thomas E. Poulsen, Box 19, Jiggs, Nev. 89827

[21] Appl. No.: 773,989

[22] Filed: Oct. 9, 1991

Related U.S. Application Data

[63] Continuation of Ser. No. 322,081, Mar. 10, 1989, abandoned.

[51] Int. Cl.$^5$ ............................................. A61M 5/32
[52] U.S. Cl. ...................................... 604/198; 604/263
[58] Field of Search ............... 604/162, 163, 192, 197, 604/198, 239, 263

[56] References Cited

U.S. PATENT DOCUMENTS

| | | | |
|---|---|---|---|
| 4,795,432 | 1/1989 | Karczmer | 604/198 |
| 4,804,371 | 2/1989 | Vaillancourt | 604/198 |
| 4,850,977 | 7/1989 | Bayless | 604/263 |
| 4,850,996 | 7/1989 | Cree | 604/263 |
| 4,863,435 | 9/1989 | Sturman et al. | 604/263 |
| 4,921,490 | 5/1990 | Spier et al. | 604/263 |
| 4,927,416 | 5/1990 | Tomkiel | 604/198 |

Primary Examiner—Stephen C. Pellegrino
Assistant Examiner—Michael Rafa

[57] ABSTRACT

The several embodiments include a hypodermic needle with a hollow member positioned over a portion of the needle, thus covering that portion of the needle. Prior to and during use, the hollow member is held away from the piercing end of the needle to allow it to be used in the normal manner. After the needle has become contaminated, a simple action by the user places the hollow member in a position covering the piercing end of the needle, and the hollow member is supported in this position against rearward pressure. The hollow member is similarly kept from sliding off the end of the needle.

34 Claims, 11 Drawing Sheets

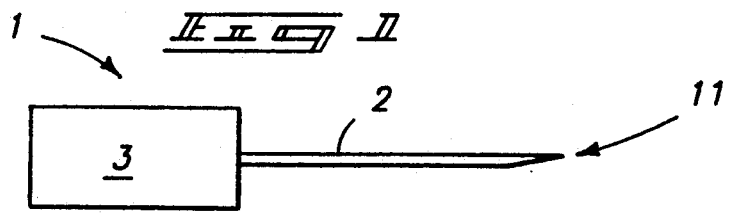
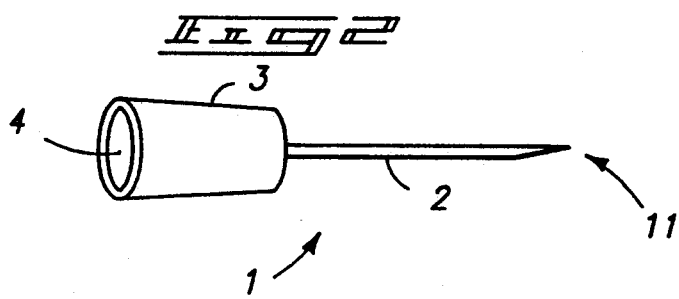
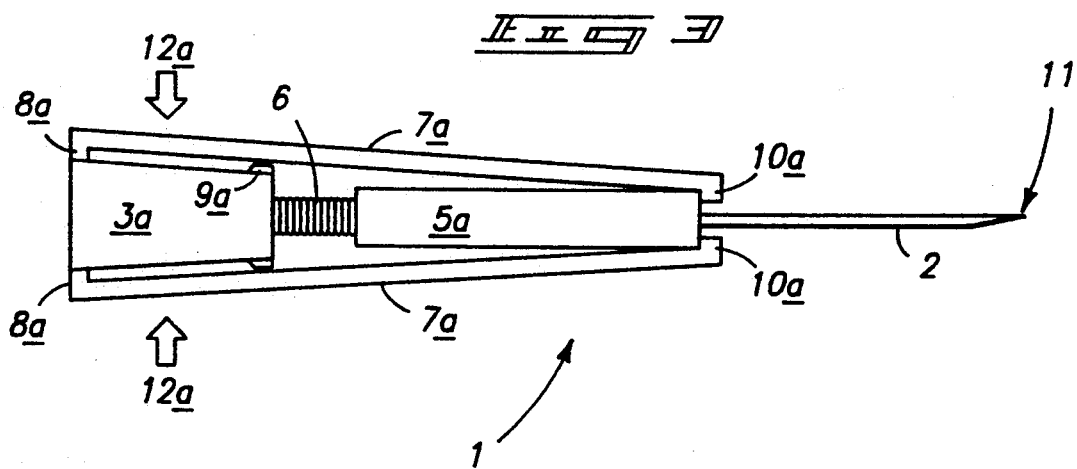
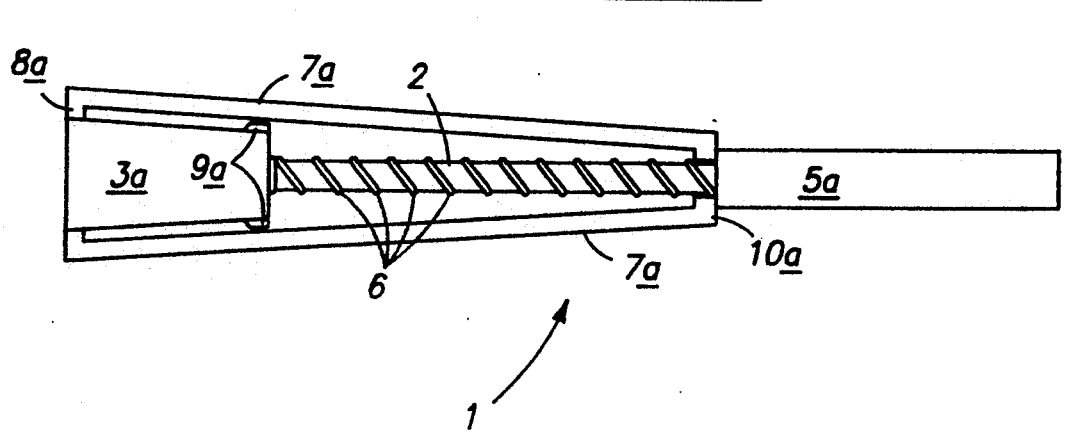

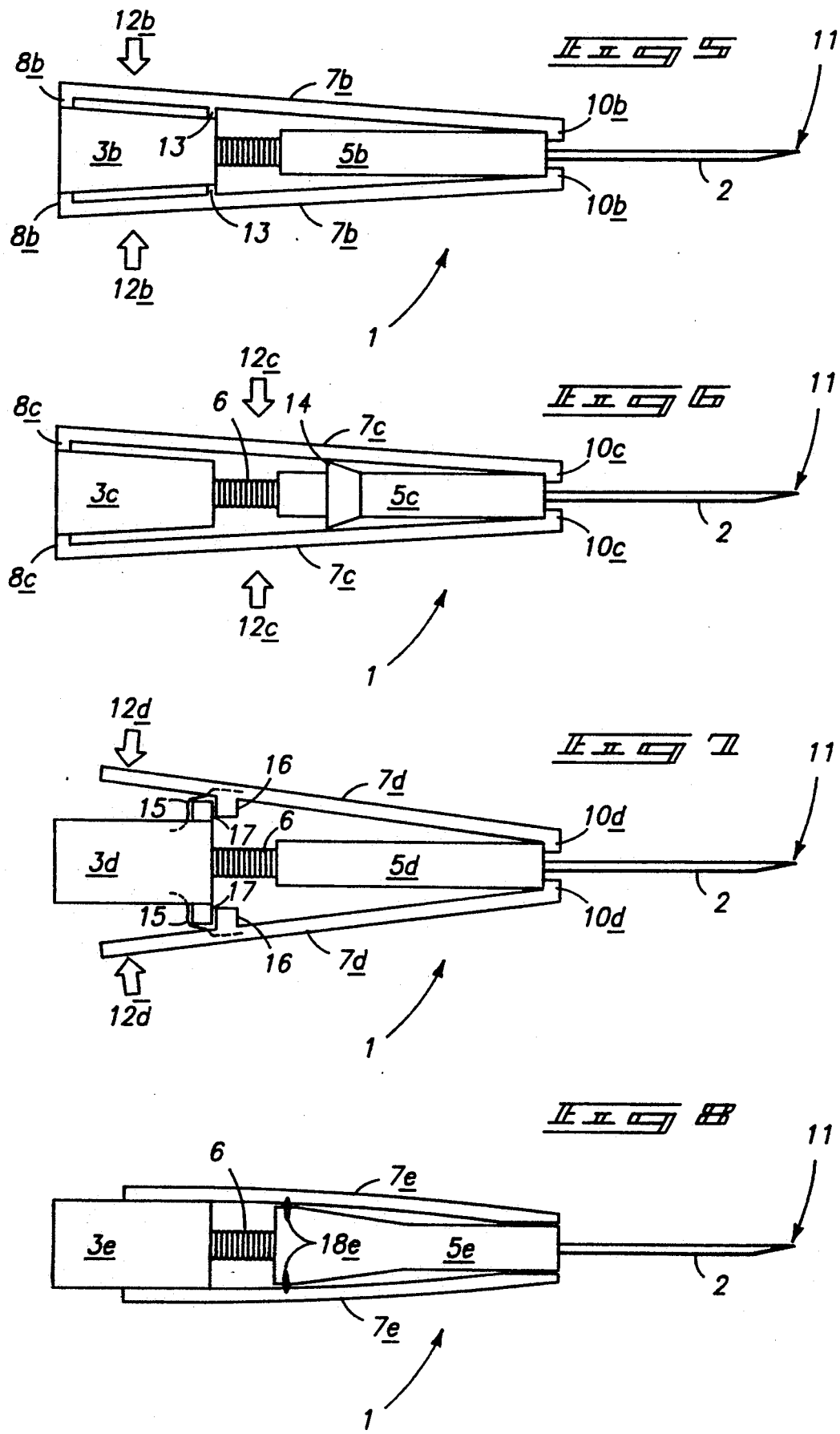

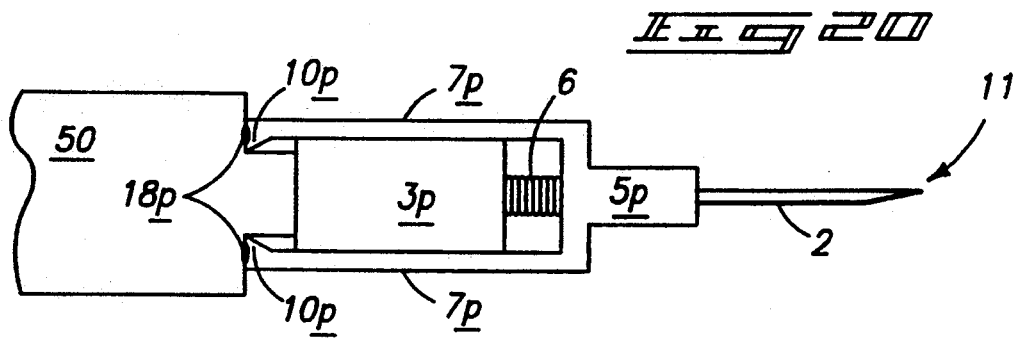
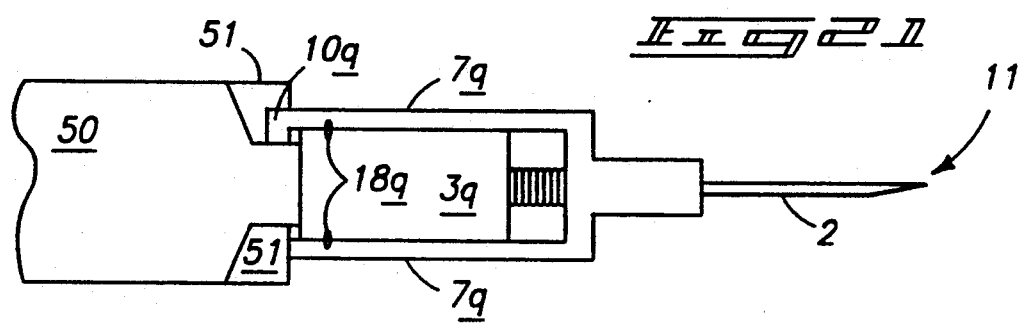
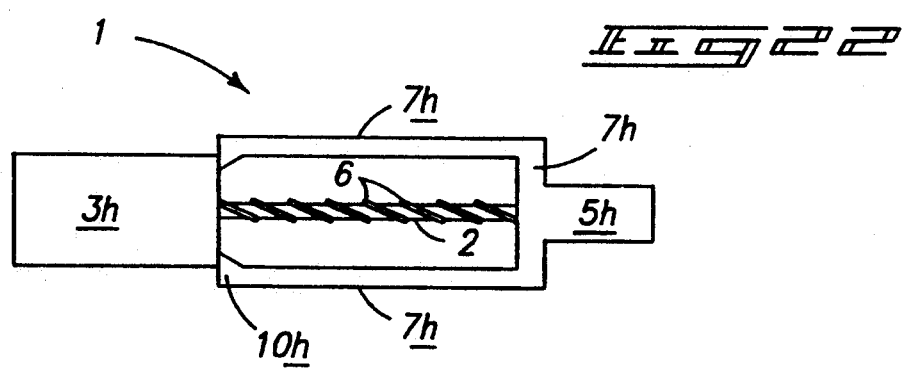
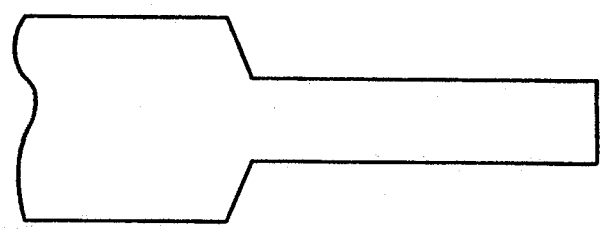

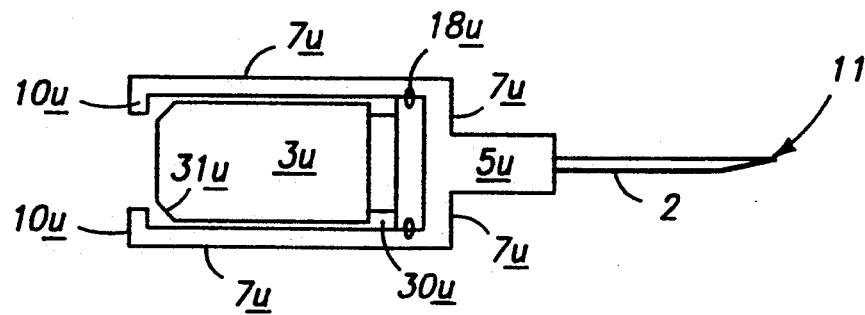
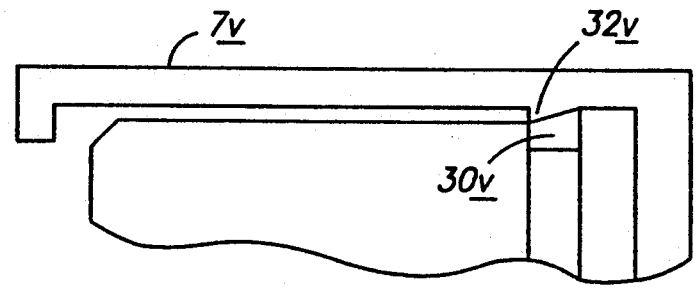
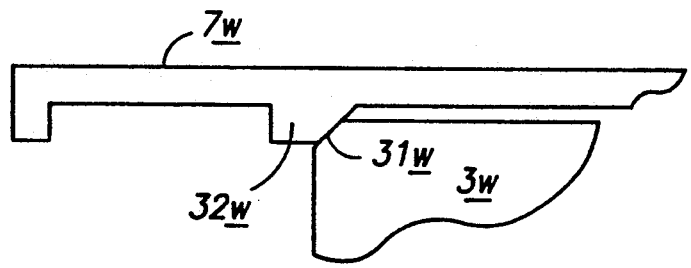
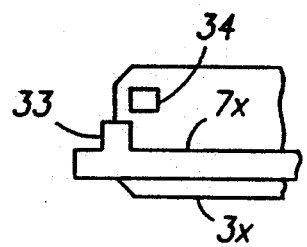

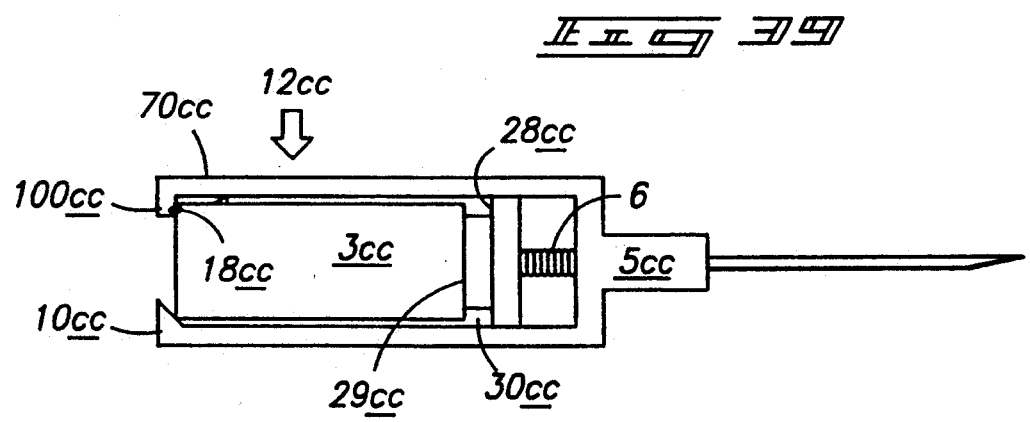

5,300,039

SAFETY HYPODERMIC NEEDLE

This application is a continuation of Ser. No. 07/822,081 filed Mar. 10, 1989, now abandoned.

BACKGROUND OF THE INVENTION

One of the major safety concerns of nurses and other health workers is the risk of accidentally pricking oneself with contaminated hypodermic needles. This concern has become particularly acute since the onset of the AIDS epidemic. It has been reported that, as of January 1989, 20 health workers have been infected by the AIDS virus by such accidental needle pricks.

In light of the dangers associated with contaminated hypodermic needles, it would be of importance to develop a hypodermic needle that is safer than existing hypodermic needles to the people who must handle them. Accordingly, it is an object of the present invention to provide a hypodermic needle that is safer than existing hypodermic needles for health workers and others to use and handle. In keeping with the proceeding object, it is also an object of this invention to develop such a hypodermic needle that is not cumbersome in use, and that can be put into the safe mode by a simple action by the health worker immediately after the needle has been removed from the patient. And in light of the large quantity of hypodermic needles that are used by the health profession, and the expense involved with this large quantity of use, it is a further object of this invention to provide such a safe, easy to use hypodermic needle that can be manufactured relatively inexpensively.

SUMMARY OF THE INVENTION

In the several embodiments, the invention includes a hypodermic needle with a hollow member positioned over the needle segment of the hypodermic needle. The hollow member covers a portion of the needle, and is capable of sliding along the needle. Prior to and while the hypodermic needle is being used, the hollow member is held away from the piercing end of the needle, thus enabling the needle to be used in the normal manner. After the needle has became contaminated, the hollow member is slid forward along the needle to cover its piercing end. The hollow member is supported in a position covering the piercing end of the needle against rearward pressure, and is similarly prevented from sliding off the end of the needle. In several of the embodiments, the hollow member is pushed forward by a spring, thus requiring only a simple action by the user to put the hypodermic needle in a safe condition for subsequent handling.

BRIEF DESCRIPTION OF THE DRAWINGS

FIG. 1 is a side view of an ordinary hypodermic needle.

FIG. 2 is a perspective view of the hypodermic needle of FIG. 1, showing the opening for receiving the syringe or I. V. attachment.

FIG. 3 is a side view of the first embodiment of the invention as it would appear before it has been used.

FIG. 4 is a side view of the embodiment of FIG. 3, showing the hypodermic needle after it has been put into the safe mode after use.

FIG. 5 shows a variation of the embodiment shown in FIGS. 3 and 4.

FIG. 6 is a side view of the second embodiment of the invention shown before use.

FIG. 7 is a side view of the third embodiment of the invention before use.

FIG. 8 is a side view of the fourth embodiment of the invention before use.

FIG. 20 shows the ninth embodiment of the invention in which a hypodermic needle and a syringe, which is shown in part, are combined as a single functioning unit.

FIG. 21, the tenth embodiment, shows the t of FIG. 11 with which a specially designed syringe, shown in part, is used for ease of operation.

FIG. 22 depicts the embodiment of FIG. 11 after the hypodermic needle has been put into the safe mode.

FIG. 23 is a partial view of a specially designed syringe with a long neck portion, to be used with some versions of some of the embodiments.

FIG. 28 is a side view of the twelfth embodiment of the invention.

FIG. 29 is a partial expanded view, from the side, of the embodiment of FIG. 28, showing a variation of that embodiment.

FIG. 30 is another partial expanded view, from the side, of the embodiment of FIG. 28, showing a variation of that embodiment.

FIG. 31 is a partial view, from the top, showing a variation of the embodiment of FIG. 28.

FIG. 39 shows an embodiment similar to that shown in FIG. 16, but where the hub includes an encircling groove.

DETAILED DESCRIPTION

Figure 9:
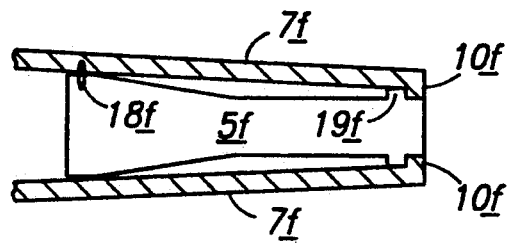
FIG. 9 is a partial side view of the embodiment of FIG. 8, showing a variation of that embodiment.

In all of the embodiments described herein, it is generally preferred that all parts other than the needles 2, springs 6, and the small pieces of spring steel 15 used in the third embodiment (FIG. 7) are formed of plastic. This preference, however, does not preclude the option of using materials other than plastic if such other materials prove advantageous to plastic either in the function of the invention, or in its manufacture.

All of the following embodiments include a hub, which is designated by the numeral 3 followed by a letter, and a hollow member, which is designated by the numeral 5 followed by a letter. Where the hubs of the various embodiments are formed of plastic as preferred, it is also preferred that all plastic parts connected directly with the plastic hubs of the various embodiments, or indirectly through a continuum of plastic, be formed with those hubs by a plastic molding process, such as injection molding. However, methods other than molding may be used to join these parts if desired. It is similarly preferred that, where the hollow members of the various embodiments are formed of plastic as preferred, all plastic parts connected directly with the hollow members, or indirectly through a continuum of plastic, be formed with those hollow members by a plastic molding process, such as injection molding. Again, however, methods other than molding may be used to join these parts if so desired.

Where the hubs of the various embodiments, are formed of plastic, the needles 2 may be attached to those plastic hubs either by being molded into the hubs in the plastic molding process as molded-in inserts, or they may be attached to the hubs after the hubs have been molded. In the latter case, they would preferably be inserted into a hole formed into the end of the hub and be secured to the hub by any of a variety of methods such as those which are described in the trade as cementation, ultrasonic installation, or press-in insertation, for example. In either case, it may be desired to have an intermediary material attached to the outside of the needle 2 where it is joined to the hub. This intermediary material would function to increase the surface area of the junction with the plastic hub, thus increasing the strength of that junction, and it may also be a material selected to join more effectively with the plastic of the hub than would the material of which the needle 2 is composed.

Most of the following embodiments include a spring 6, and in most embodiments where a spring 6 is used, those springs 6 are connected at one end with the hub, and at the other end with the hollow member. Insofar as those hubs and/or hollow s are formed of plastic, the preferred methods of attachment of the spring 6 with the hub, and the spring 6 with the hollow member are the same as between needle 2 and hub; that is, being molded in as molded-in inserts, ultrasonic installation, and cementation. The method of attaching the spring 6 may, of course, vary between the hub and the hollow member. Where the hub and/or the hollow are not formed of plastic, cementation may still be employed as a means of attaching the spring 6 to the hub and/or the hollow member.

The conventional portion of the hypodermic needle 1 is composed of the needle 2 and the hub 3. FIGS. 1 and 2 depict a conventional hypodermic needle 1. As shown in FIG. 2, one end of the hub 3 includes an opening 4 which accepts the syringe or I.V. attachment.

In the first embodiment of the present invention, illustrated in FIG. 3, a hollow member 5A is positioned over a length of the needle 2. A spring 6 is positioned between the hub 3A and the hollow member 5A, encircling the needle 2. The spring 6 is connected at one end to the hollow member 5A, and at the other end to the hub 3A. Two supporting members 7A extend from the rear of the hub 3A toward the piercing end 11 of the needle 2, each of the two supporting members 7A being located approximately 180° from the other around the hub 3A. The supporting members 7A are connected to the hub 3A by bridges 8A. At the forward end of the hub 3A two protrusions 9A extend outward from the hub 3A, so that a protrusion 9A is located directly beneath each of the supporting members 7A; the protrusions 9A are not connected to the supporting members 7A. At the forward end of each of the supporting members 7A a stop 10A extends inward from the supporting members 7A toward the needle 2. The stops 10A hold the hollow member 5A away from the piercing end 11 of the needle 2 against tension from the spring 6.

While in use, the hypodermic needle 1 is generally safe from contamination prior to its being inserted into the patient. It is after the needle has been removed that it is potentially hazardous to others. In practice, the person removing the hypodermic needle 1 of the first embodiment from the patient squeezes inwardly on the two supporting members 7A, preferably with his or her thumb and forefinger, between the bridges 8A and the protrusions 9A at a position indicated generally by the arrows 12A. In response to this inward movement, the two protrusions 9A act as fulcrums to the supporting members 7A, causing the forward end of the supporting m s 7A and the stops 10A to move outward away from the needle 2. This movement releases the hollow 5A, causing it to move forward by the force of the spring 6 to cover the piercing end 11 of the needle 2. After the hollow 5A has passed the stops 10A, and finger pressure on the supporting members 7A has been released, the forward ends of the supporting members 7A move inward toward the needle 2 in order to retain their natural position. This places the stops 10A behind the hollow member 5A, and thereby prevents the hollow member 5A from being accidentally pushed rearward exposing the piercing end 11 of the needle 2, as illustrated in FIG. 4.

FIG. 5 depicts a slight variation of the first embodiment in which the protrusions 9A of FIGS. 3 and 4 are replaced with forward bridges 13. The forward bridges 13 are connected to the hub 3B and the supporting members 7B, and are thinner than the protrusions 9A of FIGS. 3 and 4 when measured longitudinally of the hypodermic needle 1. When squeezing inwardly on the supporting members 7B at a position indicated generally by the arrows 12B of FIG. 5, the forward bridges 13 are thin enough to bend rearward while acting as fulcrums for the supporting members 7B. This enables the front of the supporting members 7B and the stops 10B to move away from the needle 2 and release the hollow member 5B.

In the second embodiment of the invention, depicted in FIG. 6, the construction is similar to the first embodiment as depicted in FIGS. 3 and 4, except that the protrusions 9A of FIGS. 3 and 4 are absent and their fraction is replaced by the ridge 14 located on the hollow member 5C (FIG. 6). When inward pressure is applied to the supporting members 7C, as with thumb and forefinger, at a position indicated generally by the arrows 12C, the ridge 14 acts as the fulcrum to the supporting members 7C, causing the forward end of the supporting members 7C and the stops 10C to move outward away from the needle 2. As a result, the hollow member 5C is released by the stops 10C and moves forward by the force of the spring 6. The inclined forward edge of the ridge 14 allows the ridge 14 to pass by the stops 10C. After the hollow member 5C has covered the piercing end 11 of the needle 2, the stops 10C lodge behind the hollow member 5C and thereby prevent the hollow member 5C from being accidentally pushed rearward, exposing the piercing end 11 of the needle 2. The advantage of the second embodiment over the first is the greater force of leverage transmitted to the outward movement of the stops, making it easier to actuate the release of the hollow member. Also, since the distance along the supporting members between the fulcrum and the stops is shorter in the second embodiment than it is in the first, that segment of the supporting members would be more rigid and less likely to bend adversely in response to the frictional resistance between the stops and the hollow member resulting from the pressure from the spring. Such bending could prevent the release of the hollow member.

In the third t depicted in FIG. 7, each of the two supporting members 7D are connected to the hub 3D with a separate piece of spring steel 15 formed from a flat elongate piece of stock. The shape of the piece of spring steel 15 and the manner in which it is connected to the hub 3D and the two supporting members 7D cause the ends of the two supporting members 7D to push inward toward the needle 2. When finger pressure is applied inwardly on the end portions of the two supporting members 7D, at a location indicated generally by the arrows 12D, the two pieces of spring steel 15 act as fulcrums to the two supporting members 7D, causing the ends of the supporting members 7D and the stops 10D to move away from the needle 2 thus releasing the hollow member 5D to move forward by the force of the spring 6. As with the previous embodiments, after the hollow member 3D has covered the piercing end 11 of the needle 2, the stops 10D move inward, toward the needle 2 by the force of the piece of spring steel 15, and lodge behind the hollow member 5D. With the stops 10D behind the hollow member 5D, and the protuberances 16 on the supporting s 7D aligned with the protuberances 17 on the hub 3D, the hollow member 5D is prevented from being pushed rearward exposing the piercing end 11 of the needle 2.

In the fourth embodiment shown in FIG. 8, two supporting members 7E extend forward from the hub 3E, curving inward toward their forward ends. The two supporting members 7E are connected with the hollow member 5E by melt seals 18E that are formed by melting plastic of the supporting members 7E together with plastic of the hollow member 3E at an isolated spot where the two are in contact, as indicated by the reference character 18E. The melt seals 18E between the supporting members 7E and the hollow 5E hold the hollow member 5E away from the piercing end 11 of the needle 2 against the tension of the spring 6. In practice, once the needle 2 has been removed from the patient, the person removing the needle 2 may perform one of several actions in order to break the melt seals 18E. In one such action the hollow member 5E is grasp, as with thumb and forefinger, and twisted relative to the supporting member 7E. Another action calls for pushing forward on the rear of the hollow member 5E, preferably with either thumb or forefinger. In still another action, the user may squeeze inwardly on the support members 7E, preferably with thumb and forefinger, as at a position between the rear of the hollow member 5E and the front of the hub 3E, behind the melt seals 18E. A similar squeezing action on the supporting members 7E forward of the metal seals 18E may also break the melt seals 18E. Once the melt seals 18E have been broken, the hollow member 5E moves forward by the force of the spring 6. The outside of the hollow member 5E flares outward, increasing in diameter toward the rear of the hollow member 5E. This flared shape allows the hollow member 5E to move past the ends of the supporting members 7E, bending the supporting members 7E outward slightly as the hollow member 5E moves forward. Once the hollow member 5E has passed the ends of the supporting members 7E and has covered the piercing end 11 of the needle 2, the ends of the supporting members 7E move back inward toward the needle 2 and lodge behind the rear surface of the hollow member 5E, preventing accidental rearward movement of the hollow member 5E. Since the supporting members 7E curve toward each other toward their fronts, the supporting members 7E are closest together at their front ends. The distance between the supporting members 7E at their front ends is less than the diameter of the rear surface of the hollow member 5E, though, the distance between the two supporting members 7E at the hub 3E is greater than the diameter of the rear surface of the hollow member 5E.

Figure 10:
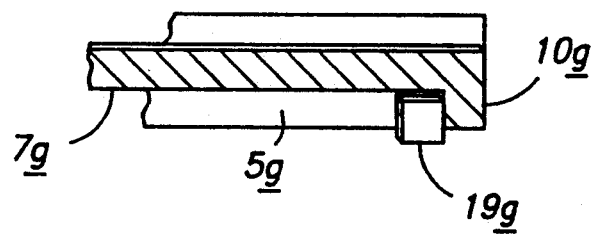
FIG. 10 is a partial view, from the top, of the embodiment of FIG. 8, showing a variation of that embodiment.

FIGS. 9 and 10 show variations of the fourth embodiment in which securement means in addition to the melt seals are used to hold the hollow member 5F against tension from the spring. FIG. 9 is a side view showing that portion of the embodiment where the variation exists. In the variation depicted in FIG. 9, a stop 10F extends inward from the end of each supporting member 7F. A projection 19F extends outward from the hollow m 5F behind each stop 10F. Twisting of the hollow member 5F relative to the supporting members 7F releases the stops 10F from the projections 19F, as well as breaking the melt seals 18F. Only one melt seal 18F is shown in FIG. 9 to indicate that the other melt seal is located on the other side of the lower supporting 7F. This allows for smoother, unobstructed forward movement of the hollow member 5F when the hollow 5F is twisted in a certain direction. Such positioning of the melt seals is an option on all embodiments where two supporting members are attached with melt seals.

FIG. 10 is a top view that also shows that part of the embodiment where the variation exists. In the variation depicted in FIG. 10, a stop 10G extends laterally from the end portion of each supporting member 7G. A projection 19G, similar or identical to the projection 19F shown in FIG. 9 extends outward from the hollow member 5G behind each stop 10G. In a manner similar to the variation depicted in FIG. 9, twisting of the hollow 5G relative to the supporting member 7G releases the stops 10G from the projections 19G as well as breaking the melt seals.

The manner in which the first version of the fourth embodiment (FIG. 8) is designed would enable the hub 3E and supporting members 7E to be formed together by a plastic molding process, such as injection molding, in a mold that, in terminology of the trade, would not require the use of slides. This should be the case either if the hub 3E and supporting members 7E are molded without the needle 2, or if the needle 2 is molded into the hub 3E as a molded-in insert. The necessity of using a mold with slides increases production costs for the item molded.

One disadvantage of the embodiments described thus far is that a large proportion of the needle 2 segment of the hypodermic needle 1 must be covered with the hollow member and spring 6 prior to and during its use. The segment of the needle 2 thus covered cannot be utilized for its intended purpose. Because of this, the hypodermic needle 1 must be constructed with a longer needle 2 segment than would otherwise be needed for any particular application.

In the following embodiments, the proportion of the needle 2 segment of the hypodermic needle 1 covered by the hollow member is kept to a minimum by a basic design change from those previous embodiments. This design change, however, does necessitate the lengthening of the hub portion of the hypodermic needle 1, except when the desired needle 2 length is relatively short, or when a specially designed syringe with a long neck is used with the hypodermic needle 1. Such a specially designed syringe is depicted, in part, in FIG. 23. Whether or not the hub must be lengthened to accommodate this design, it would likely be more economical to increase the length of the hub, especially if the hub is formed of plastic, than it would be to increase the length of the steel needle 2 segment of the hypodermic needle 1.

In the several following embodiments, the two supporting members are attached to the hollow member rather than the hub. In the fifth embodiment of the invention depicted in FIG. 11, two supporting members 7H are connected with the hollow member 5H and extend rearward from the hollow member 5H. A stop 10H is located at the rear of each supporting member 7H. The supporting members 7H are connected to the hub 3H with melt seals 18H, which hold the hollow member 5H away from the piercing end 11 of the needle 2 against tension from the spring 6. The hollow member 5H is released by a twist of the supporting members 7H, preferably with thumb and forefinger, in a short circular motion around the outside of the hub 3H, which breaks the melt seals 18H. The inclined forward portion of the stops 10H allow the stops 10H to move past the end of the hub 3H as the hollow member 5H moves forward by the force of the spring 6. After the hollow member 5H has covered the piercing end 11 of the needle 2, the stops 10H lodge in front of the hub 3H. This prevents accidental rearward movement of the hollow member 5H exposing the piercing end 11 of the needle 2, as shown in FIG. 22. FIG. 12 depicts another example of this same embodiment where a longer needle segment is used, necessitating a longer hub. The dashed line 21 indicates the rear border of a shorter hub that could be used if the hypodermic needle is used with a specially designed syringe with a long neck, as the syringe depicted, in part, in FIG. 23.

Figure 13:
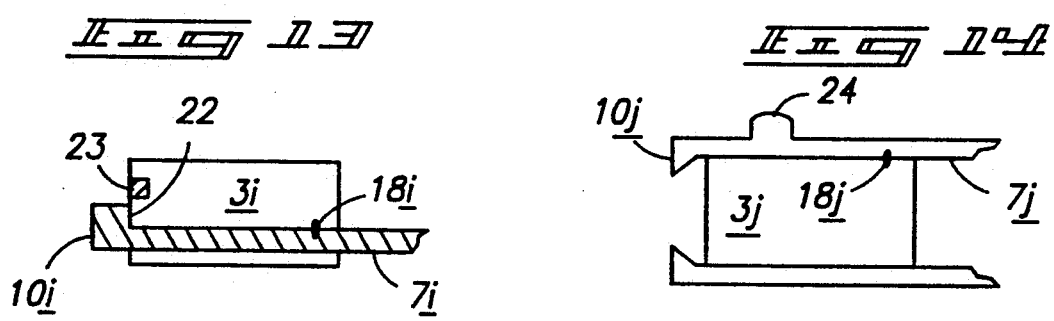
FIG. 13 is a partial view, from the top, of the embodiment of FIGS. and 12, showing a variation of that embodiment.

FIG. 13 shows a top view of the hub section in a slight variation of the fifth embodiment. The variation involves widening the rear portion of the supporting members 7I, including the stops 10I, to form a step 22. Two projections 23 extend outward at the rear portion of the hub 3I, each projection 23 being aligned with the step 22 on one of the supporting members 7I. The steps 22 with the projections 23 provide additional securement, along with the melt seals 18I, in holding the hollow member rearward against tension of the spring. The same twisting motion of the supporting members 7I described initially for the fifth embodiment releases the steps 22 from the projections 23, as well as breaking the melt seals 18I to release the hollow member. Of course, with this variation, one or more of the melt seals 18I could be eliminated, or the projection 23 and step 22 may be utilized on only one of the supporting members 7I. FIG. 13 shows the hub as it would appear after the step 22 on the supporting members 7I has been twisted free of the projection 23.

Figure 14:
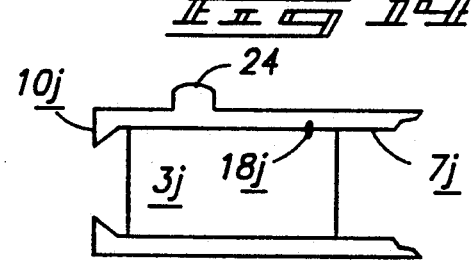
FIG. 14 is a partial side view of the embodiment of FIGS. 11 and 12, showing a variation of that embodiment.

FIG. 14 shows the hub section of another variation of the fifth embodiment. In this example, only one of the two supporting members 7J is secured to the hub 3J with a melt seal 18J. That same supporting member 7J includes a knob 24 on its top. Release of the hollow member is actuated by pushing forward on the knob 24 as with thumb or forefinger, and thus breaking the melt seal 18J.

Figure 15:
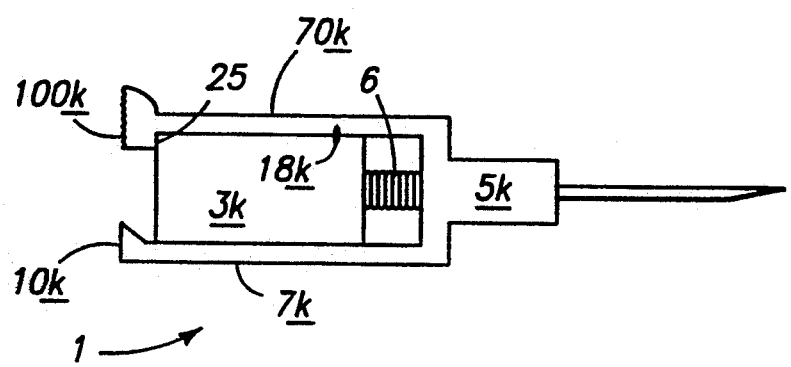
FIG. 15 is a side view of the sixth embodiment of the invention before use.

In the sixth embodiment, depicted in FIG. 15, a flat front surface 25 on one of the stops 100K rests against the rear of the hub 3K. This helps support the hollow member 5K against the tension of the spring 6. The same supporting member 70K on which the stop 100K is located is attached to the hub 3K with a melt seal 18K. The other supporting 7K is not attached to the hub 3K. Thumb or finger pressure on the rear of the stop 100K, pushing upward and forward, releases the stop 100K from the hub 3K allowing the hollow member 5K to spring forward. Both stops 100K and 10K align with the front of the hub 3K to prevent accidental rearward movement of the hollow member 5K.

Figure 16:
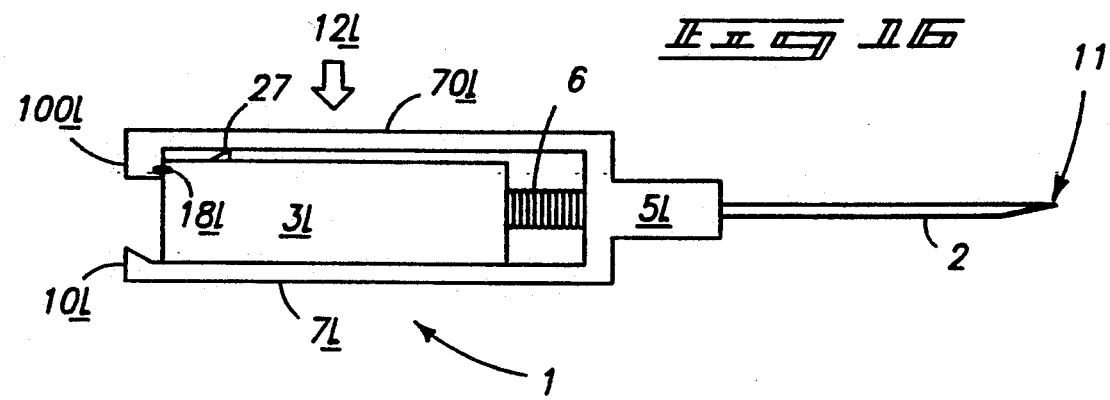
FIG. 16 is a side view of the seventh embodiment of the invention before use.

In the seventh embodiment depicted in FIG. 16, a flat front surface on one of the stops 100L rests against the rear of the hub 3L. A ridge 27 extends outward from the hub 3L directly underneath the supporting member 70L. The supporting member 70L is held away from the hub 3L except at the ridge 27. A melt seal 18L connects the stop 100L with the hub 3L. The melt seal may alternately be located between the supporting member 70L and the ridge 27, or may be eliminated altogether. The other supporting member 7L is not sealed to the hub 3L. The release the hollow member 5L, a person pushes inward and forward on the supporting 70L, at a position forward of the ridge 27, at a location indicated generally by the arrow 12L. The inward movement of the supporting member 70L at this location causes the stop 100L to move outward in relation to the hub 3L, and together with the forward movement causes the stop 100L to be released from the hub 3L. The melt seal 18L is broken in the process, and the hollow 5L moves forward to cover the piercing end 11 of the needle 2. After lodging in front of the hub 3L, the stops 100L and 10L prevent rearward movement of the hollow member 5L.

Figure 17:
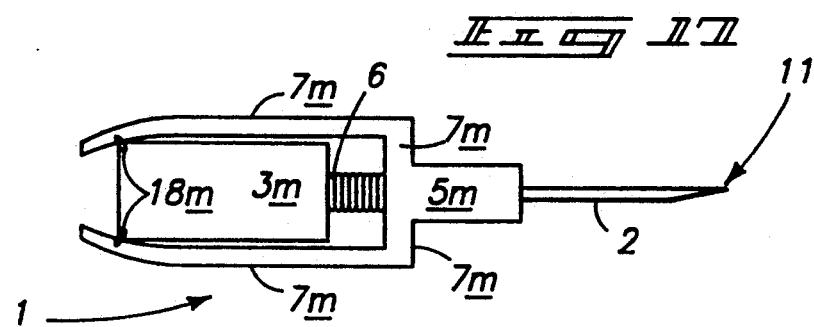
FIG. 17 is a side view of the eighth embodiment of the invention before use.
Figure 19:
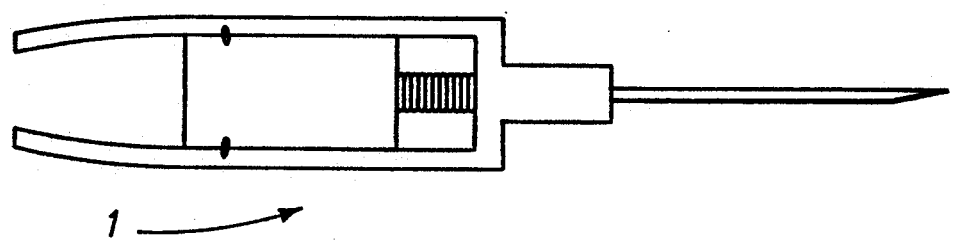
FIG. 19 shows the embodiment of FIG. 17 with a longer needle.

The eighth t is shown in FIGS. 17 and 19, wherein FIG. 19 depicts a version with a longer needle to be used with a syringe with a long neck, such as the syringe shown, in part, in FIG. 23. In this embodiment the supporting members 7M curve inward toward the rear so that the supporting members 7M are closest together at their ends. The supporting members 7M are connected with the hollow member 5M and are connected to the hub 3M with the melt seals 18M. A short twisting of the supporting members 7M around the periphery of the hub 3M (as in the fifth embodiment) causes the melt seals 18M to break. Another action by which the melt seals 18M may be broken is squeezing inwardly on the supporting members 7M, preferably with thumb and forefinger, as at a location just forward of the melt seals 18M, or, alternately, just rearward of the melt seals 18M. Once broken, the hollow member 5M travels forward by the force of the spring 6, bending the end portions of the supporting members 7M outward slightly as they pass the hub 3M. Since the distance between the ends of the supporting members 7M is less than the diameter of the front surface of the hub 3M, the ends of the supporting members 7M lodge in front of the hub 3M after the hollow member 5M has covered the piercing end 11 of the needle 2, preventing rearward movement of the hollow member 5M.

Figure 18:
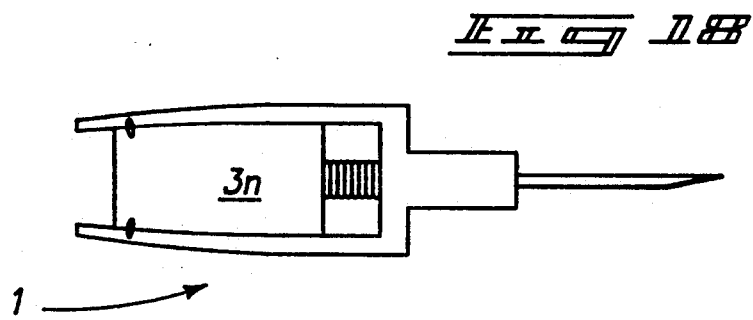
FIG. 18 shows a variation of the embodiment shown in FIG. 17.

FIG. 18 depicts a slight variation of this embodiment in which the hub 3N is formed to flare outward toward the front, so that the diameter of the front surface of the hub 3N is greater than the diameter of the rear of the hub 3N.

The manner in which the eighth embodiment is designed would enable the hollow member 5M, and the supporting members 7M to be formed together by a plastic molding process, such as injection molding, in a mold that would not require the use of slides.

Occasionally, a hypodermic needle and a syringe are packaged as a single unit, such as to dispense a specified quantity of medicine. In the ninth embodiment, depicted in FIG. 20, a hypodermic needle/syringe combination is shown in which the two fraction as a single disposable unit to carry out the primary object of this invention. Melt seals 18P attach the stops 10P to the syringe 50 to hold the hollow member 5P against tension from the spring 6. A twist of the syringe 50 with one hand while holding the hub 3P of the hypodermic needle with thumb and forefinger of the other hand, breaks the melt seals 18P allowing the hollow 5P to move forward. The presence of the thumb and forefinger on the hub 3P prevents the supporting members 7P from simply turning with the syringe 50, rather than breaking. The relatively wide syringe 50 offers a sturdy grip for the user to twist.

Figure 11:
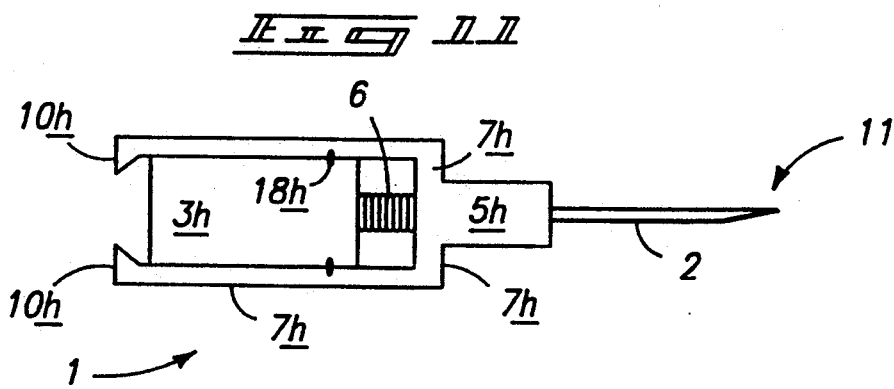
FIG. 11 is a side view of the fifth embodiment of the invention shown before use.
Figure 12:
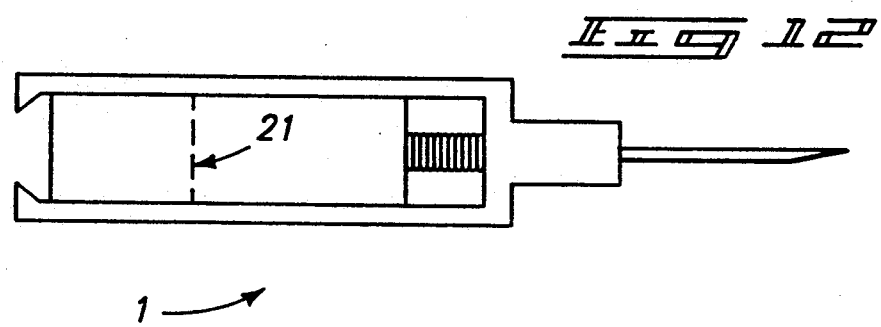
FIG. 12 shows the embodiment of FIG. 11 with a longer needle, and, in one alternate, a longer hub.

Although the hypodermic needle shown in this embodiment is essentially identical to the one depicted in FIG. 11, any of those previous embodiments in which the hollow member is released by twisting the supporting s may be used in combination with the syringe in the manner just described and shown in FIG. 20.

In the tenth embodiment as depicted in FIG. 21, a specially designed syringe is used with a separate hypodermic needle. As was the case for the embodiment depicted in FIG. 20, the hypodermic needle used in this example is essentially identical to the one depicted in FIG. 11, though any of those previously described hypodermic needles in which the hollow member is released by twisting the supporting s may be used with this type of syringe. Flaps 51 extending forward on the syringe 50 match with the ends of the supporting members 7Q and stops 10Q of the hypodermic needle. A twist of the syringe 50 while thumb and forefinger grasp the hub 3Q causes the flaps 51 to rotate the supporting members 7Q, thus breaking the melt seals 18Q. The flaps 51 of this syringe 50 may be combined with a long neck, as on the syringe depicted in FIG. 23, to be used with those hypodermic needles designed to be used with long neck syringes. In such a combination, it would likely be desirable to extend the flaps 51 of FIG. 21 further forward as well.

Figure 24:
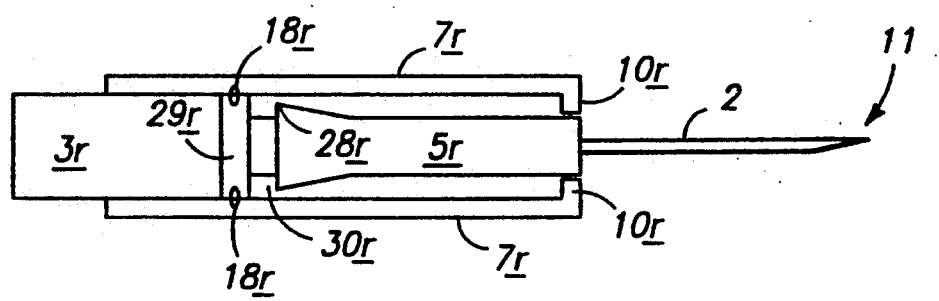
FIG. 24 is a side view of the eleventh embodiment of the invention. No spring is used in this embodiment.
Figure 25:
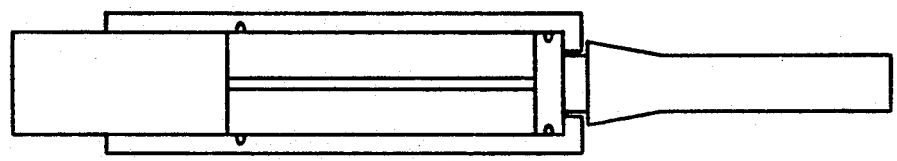
FIG. 25 shows the embodiment of FIG. 24 after it has been put into the safe mode.

In the eleventh and twelfth embodiments, depicted in FIGS. 24 through 31, a hollow member similar to those employed in the previous embodiments is pushed forward by the user, rather than by a spring. In the eleventh embodiment, depicted in FIG. 24, a front ridge 28R and a rear ridge 29R encircle the hollow member 5R to form an encircling groove 30R. Melt seals 18R connect the rear ridge 29R with the two supporting members 7R that extend forward from the hub 3R, and a stop 10R extends inward from the end of each supporting member 7R. In practice, the user breaks the melt seals 18R either by twisting the hollow member 5R relative to the supporting members 7R, or simply by pushing the hollow member 5R forward. After the melt seals 18R have been broken, the user pushes, or continues to push, the hollow member 5R forward toward the piercing end 11 of the needle 2. The inclined forward surface of the front ridge 28R allows the hollow member 5R to pass by the stops 10R, bending the supporting members 7R outward slightly, until the groove 30R reaches the stops 10R, whereupon the supporting s 7R spring inward pushing the stops 10R into the groove 30R. once the stops 10R are positioned in the groove 30R the hollow member 5R is Prevented from moving rearward exposing the piercing end 11. Of the needle 2, or from moving forward off the end of the needle 2, as shown in FIG. 25.

Figure 26:
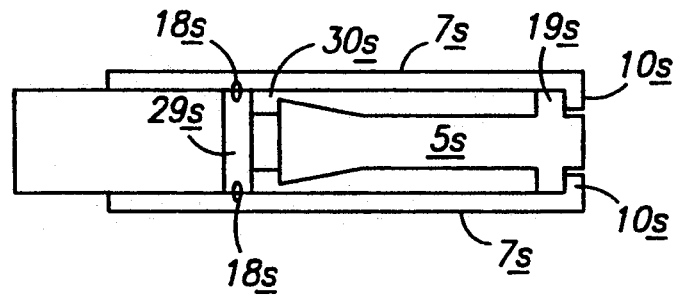
FIG. 26 shows a variation of the embodiments of FIGS. 24 and 25.
Figure 27:
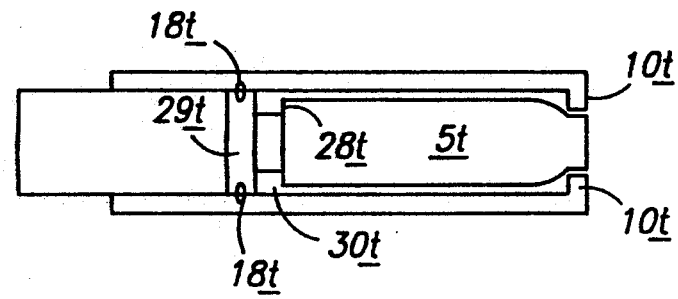
FIG. 27 shows another variation of the embodiments of FIGS. 24 and 25.

In a variation of the eleventh embodiment depicted in FIG. 26, a projection 19S extends outward from the hollow 5S behind each stop 10S to help prevent accidental breakage of the melt seals. Twisting of the hollow member 5S relative to the supporting members 7S breaks the melt seals 18S and releases the projections 19S from the stops 10S, allowing the hollow member 5S to be pushed forward. FIG. 27 depicts another variation of the eleventh embodiment in which the front ridge 28T extends to the rear of the stops 10T. In this variation, the front ridge 28T is very wide and is flat on its outer surface, and is convex just behind the stops 10T. In the variation depicted in FIG. 27, the melt seals 18T may, if desired, be eliminated altogether.

FIG. 28 depicts the twelfth embodiment in which supporting members 70 extend rearward from the hollow member 5U. A stop 10U extends inward from the end of each supporting member 7U. The outside rear edge of the hub 3U is inclined 31U to allow passage of the stop 10U. A groove 30U encircles the hub 3U near the front of the hub 3U, and melt seals 18U temporarily connect the supporting is 7U with the hub 3U. In this example, the portion of the hub 3U located forward of the groove 30U extends outward slightly more than the portion of the hub 3U located behind the groove 30U. Twisting or pushing of the supporting members 7U or hollow member 5U breaks the melt seals 18U, allowing the hollow member 5U to be pushed forward to cover the piercing end 11 of the needle 2. As forward movement proceeds, the supporting members 7U bend outward as the stops 10U move up the inclined 31U rear outside edge of the hub 3U, and subsequently spring inward as the stops 10U reach the groove 30U. Once in the groove 30U, the stops 10U prevent forward and rearward movement of the hollow member 5U, which now covers the piercing end 11 of the needle 2.

The twelfth embodiment may be adapted for a longer needle 2 by lengthening the hub 3U and supporting s 7U, or by lengthening only the supporting s 7U whereupon it would be used with a long neck syringe, as the syringe depicted in FIG. 23. The melt seals 18U may, if desired, be eliminated in this embodiment in those versions where the stops 10U rest directly or nearly directly behind the inclined 31U rear outside edge of the hub 3U. The melt seals 18U may also be eliminated, if desired, in the variations of this embodiment depicted, in part, in FIGS. 29 and 30. In FIG. 29, a protuberance 32V extends inward from one or both supporting members 7V into the groove 30V. The inclined front of the protuberance 32V allows the protuberance 32V to be pushed out of the groove 30V. In FIG. 30, the protuberance 32W extends inward from one or both supporting members 7W directly behind the inclined 31W rear outside edge of the hub 3W. The example as depicted in FIG. 30 is designed for use with a long neck syringe, as the syringe in FIG. 23. The inclined front of the protuberance 32W allows the protuberance 32W to be pushed up the inclined 31W outside rear edge of the hub 3W, and past the groove (not shown).

FIG. 31 depicts a top view of another variation of the twelfth embodiment in which a protrusion 33 extends laterally from each supporting member 7X. A projection 34 extends outward from the hub 3X in front of each protrusion 33. Alignment of the protrusions 33 and the projections 34 helps to prevent accidental breakage of the melt seals. Twisting of the supporting members 7X relative to the hub 3X breaks the melt seals and releases the protrusions 33 from the projections 34, allowing the hollow member to be pushed forward. The presence of the protrusions 33 and the projections 34 allow the option of eliminating the melt seals.

In the eleventh and twelfth embodiments, and in the variations of the eleventh and twelfth embodiments, springs may be added between the hubs and the hollow members in order that those embodiments may fraction in the same manner as the first through tenth embodiments, in that the hollow members, once released, would move forward by the force of such springs rather than by being pushed by the user. Of course, the exact structure of those embodiments as shown in the figures would generally be modified in order to accommodate the presence of the spring. For example, the supporting member may be lengthened or the hollow member shortened, relative to the other. The springs may or may not be attached to the hubs and/or hollow members since, once in the groove (the groove designated by 30 followed by a letter), the stops (10 followed by a letter) would prevent forward as well as rearward movement of the hollow member, thus preventing the hollow member from sliding off the end of the needle 2. The fact that the spring need not necessarily be attached to the hollow member and/or the hub may constitute an advantage over those previous embodiments where springs were used, that advantage being a possible lower cost of manufacture. When used with springs, the twelfth embodiment as depicted in FIG. 28 may be used in combination with the syringe of FIG. 20 (without the melt seals 18U), and with the syringe of FIG. 21. The variation of the twelfth embodiment as depicted in FIG. 31 may also be used in combination with the syringes of FIGS. 20 and 21.

Figure 35:
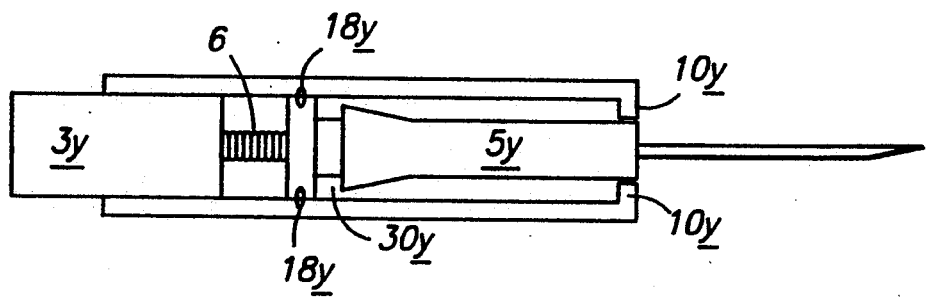

FIG. 35 depicts an embodiment similar to that shown in FIG. 24 but where a spring 6 is used to push the hollow member 5Y forward once the seals 18Y are broken. The seals 18Y may be melt seals as described above, or they may be a seal formed in a different manner, such as by the addition of a small amount of adhesive, as melted plastic (from another source), for example. Positioning of the stops 10Y in the groove 30Y prevents rearward or forward movement of the hollow member 5Y.

Figure 36:
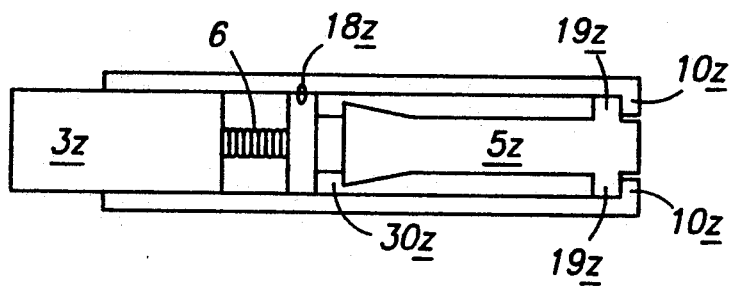
FIG. 36 is a side view of an embodiment similar to that shown in FIG. 26, but with a spring added.

FIG. 36 shows an embodiment similar to that shown in FIG. 26 but with a spring 6 added. In addition to the positioning of the stops 10Z in front of the projections 19Z, the seal 18Z helps prevent accidental release of the hollow member 5Z as well as indicating that the needle has not been used. Again, once the stops 10Z lodge in the groove 30Z the hollow member 5Z is prevented from moving rearward or forward.

Figure 37:
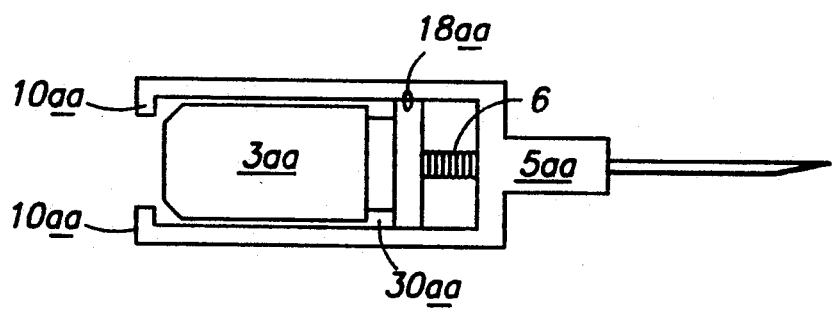
FIG. 37 is a side view of an embodiment similar to that shown in FIG. 28 with the addition of a spring.

FIG. 37 depicts the embodiment of FIG. 28 but where a spring 6 pushes the hollow member 5AA forward once the seal 18AA has been broken. Positioning of the stops 10AA in the groove 30AA prevents rearward or forward movement of the hollow member 5AA. Variations to this embodiment (with a spring) include those depicted in FIG. 29, 30 and 31.

In the embodiments depicted in FIGS. 35, 36 and 37 the spring 6 need not (if desired) be attached to either the hub or hollow member.

It will also be noted that the hollow member of FIGS. 24, 26 and 27 may be employed in the first, second, and third embodiments (FIGS. 3, 4, 5, 6 and 7), or with the first variation of the fourth embodiment (FIG. 9), in place of the hollow members used in those embodiments. When so employed, the stops of those first 3 embodiments (10A, 10B, 10C, and 10D including the variation) or the stop 10F of FIG. 9 would hold the hollow member away from the piercing end of the needle by lodging in front of the hollow member 5R of FIG. 24, in front of the projections 19S of FIG. 26, or in front of the convex forward edge of the (wide) front ridge 28T on the hollow member 5T of FIG. 27. Melt seals may or may not be used in these combinations, depending on the particular application and preference. After the hollow member has been released, those stops 10A, 10B, 10C, 10D, or 10F would lodge in the groove 30R, 30S, or 30T of FIGS. 24, 26, and 27 respectfully, preventing forward as well as rearward movement of the hollow member. When the hollow members 5R, 5S, or 5T of FIGS. 24, 26, or 27 respectfully are used with any of the first four embodiments, in place of those hollow members described for use with those embodiments, the spring 6 may or may not be attached to the hub and/or hollow member. The spring 6 may also be eliminated altogether, though use without the spring 6 is best suited for the variation of the fourth embodiment (FIG. 8) depicted in FIG. 9. When used without a spring, melt seals may or may not be used, again, depending on the particular application and preference. When the hollow members 5R, 5S, or 5T are used in combination with the second embodiment (FIG. 6), the rear ridge 29R, 29S, or 29T of the hollow members 5R, 5S, and 5T respectfully would act as the fulcrum to the supporting s 7C of FIG. 6 in place of the ridge 14 as initially described for that function in that embodiment.

Also, the sixth and seventh embodiments (FIGS. 15 and 16 respectfully) may employ a hub with a groove, as the groove 30U depicted in FIG. 28, though such a groove would have to be wide enough to accommodate the stop 100k of FIG. 15, or the stop 100L of FIG. 16. With the stop 100K of FIG. 15, or the stop 100L of FIG. 16 lodged in a groove in the hub as the groove 30U of FIG. 28, the hollow would be prevented from moving rearward or forward. Tn this combination, a spring as the spring 6 may or may not be used, and if used, the spring may or may not be attached to the hub and/or hollow member. The use of melt seals is also optional in these combinations, both with and without the use of a spring.

Figure 38:
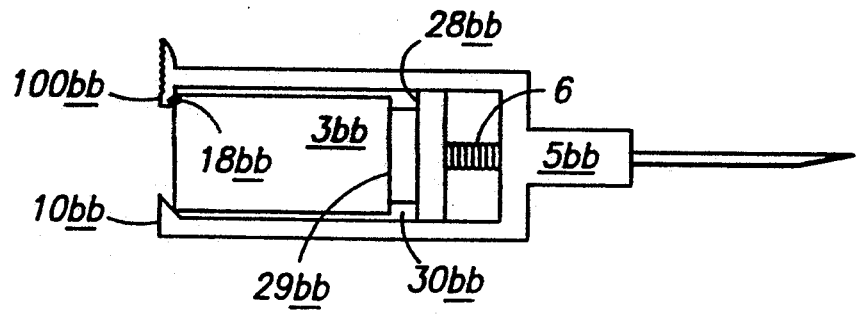
FIG. 38 shows an embodiment similar to that shown in FIG. 15, but where the hub includes an encircling groove.

FIG. 38 depicts an embodiment similar to that shown in FIG. 15 but where the hub 5BB includes an encircling groove 30BB. As is the case with the embodiments of FIGS. 37 and 39, the ridge 28BB in front of the groove 30BB is higher than the ridge 29BB in the rear of the groove 30BB. Once the stop 100BB has been lifted over the rear of the hub 3BB, and the seal 18B has been broken, the spring 6 pushes the hollow member 5BB forward until the stop 100BB lodges in the groove 30BB, thus preventing rearward or forward movement of the hollow member 5BB. The other stop 10BB also helps prevent rearward movement of the hollow member 5BB. In this embodiment, the spring 6 need not be attached to either the hub 3BB or hollow member 5BB.

FIG. 39 depicts an embodiment similar to that shown in FIG. 16 but where the hub 3CC includes an encircling groove 30CC. Pushing downward and forward on the supporting member 70CC, as at 12CC, causes the stop 100CC to move upward over the rear of the hub 3CC, while breaking the seal 18CC in the process. The spring 6 pushes the hollow member 5CC forward until the stop 100CC lodges in the groove 30CC, thus preventing forward or rearward movement of the hollow member 5CC. The other stop 10CC aids in preventing rearward movement of the hollow member 5CC. Again, the spring 6 need not be attached to either the hub 3CC or the hollow member 5CC.

In one more combination of features used in the various embodiments, it will be noted that the knob 24 of FIG. 14 may be used in combination with the twelfth embodiment depicted in FIG. 28, and the variations of the twelfth embodiment depicted in FIGS. 29 and 30. The knob 24 of FIG. 14 may also be used in the seventh embodiment depicted in FIG. 16, the knob 24 being located on the supporting member 70L at a location indicated generally by the arrow 12L. of course, the knob 24, or a similar feature may be used to increase one's grip on a supporting member of any embodiment where one or more supporting s are released by pushing or twisting.

In a number of the proceeding embodiments a melt seal was described to form a breakable connection between plastic components. As explained earlier, the melt seal is formed by melting plastic from the two components together at a spot where the two are in contact with each other. The seal so formed is broken as the user is putting the hypodermic needle in the safe mode. As described thus far, the melt seal has been used to hold the hollow member away from the piercing end of the needle against tension from the spring, and to prevent accidental release of the hollow where another means is also used to hold the hollow member away from the piercing end of the needle. Another fraction of the melt seal is to assure users that, if unbroken, the hypodermic needle has probably not been used, and, if broken, the hypodermic needle is likely contaminated even though the hollow member may have been repositioned away from the piercing end of the needle. For these two latter fractions, the melt seal may be used on those embodiments previously described where its use was not included in that description. For example, a melt seal may be used in the first embodiment (FIGS. 3 and 4) between the protrusions 9A and the supporting members 7A, or between the stops 10A or supporting s 7A and the hollow member 5A; in the second embodiment (FIG. 6) between the supporting members 7C and the ridge 14, or between the stops 10C or ends of the supporting members 7C and the hollow member 5C; and in the third embodiment (FIG. 7) between the protuberances and the protuberances 17, or between the stops 10D or end of the supporting members 7D and the hollow member 5D.

Where the melt seal has been described to hold one next to another, it may be used on both sides of that component. For example, in the various embodiments where a supporting member has been described as being attached to a hub or a hollow with a melt seal, the supporting member may be attached to that hub or hollow member with melt seals on both sides of the supporting member. Also, where two identical or similar components, such as supporting members, have been described as being attached to another component with a melt seal, only one of those two may be so attached, if desired, in order to make it easier to break free. Finally, the melt seal itself may be replaced with a feature of similar function. A small amount of an adhesive, for example, could replace the fraction of the melt seal in forming a breakable connection between two components, whether or not those components are formed of plastic.

Although all embodiments herein described utilized two supporting members, all of these embodiments, and variations thereof, are adaptable to be used with only one such supporting member. Besides lowering manufacturing costs, the use of only one supporting may result in making some or all of the embodiments easier to use, since there would be less crowding together of the various members, possibly making operation with one's fingers easier.

Figure 32:
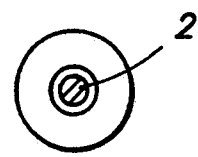
FIG. 32 is a cross-sectional view of a hollow member, showing the hole through the hollow member, with the needle in the hole.
Figure 33:
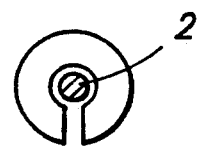
FIG. 33 is a cross-sectional view of another hollow member wherein the hole, or groove, is open to a side of the hollow member as well as the ends. The needle is shown inside.
Figure 34:
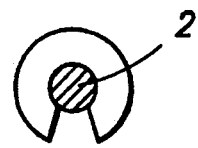
FIG. 34 is a cross-sectional view of a hollow member of similar structure to that depicted in FIG. 33. The needle is shown in FIG. 35 is a side view of an embodiment similar to that shown in FIG. 24, but with a spring added.

Health workers sometimes use a small disposable device in which to prick a finger in order to take a single drop of blood for a sample. A device called a lancet is used for this purpose. The various embodiments of this invention are adaptable to such a device, or a device designed for such a function. Of course, a hollow needle capable of transmitting fluids need not be used in this fraction, nor would a hub designed to transmit fluids to or from a syringe. To perform such a function, a round sharply pointed needle that is not necessarily hollow, or a flat sharply pointed blade-like member may be attached to a handle with the essential outer characteristics of the various hubs described herein. All of the other features described for the various embodiments, and variations of those embodiments, would be used in adapting any one embodiment, or variation thereof, to this fraction; again, all features except the fluid transmitting means of the needle and hub. Of course, certain modifications of the various members may be necessary. For example, if a flat blade-like member is used as the piercing member, the hole through the hollow member would have a conforming shape. If a spring is used to push the hollow forward, that spring should, preferably, have a conforming shape around the periphery of that blade-like The hole passing through the hollow s may be of varying character, as those depicted in FIGS. 32, 33 and 34. FIGS. 32, 33 and 34 are cross-sectional views of hollow members with the needle 2 included. The structures depicted in FIGS. 33 or 34, or a similar grooved construction, may prove advantageous in the manufacture of the hollow members in some or all of the embodiments, especially when those hollow members are formed of plastic.

The invention herein described, including all embodiments and variations of those embodiments, and including the various functions thereof, can be used in either human or veterinary medicine for use on either humans or animals.

Also, where a hypodermic needle and a syringe are combined as a single unit, any of the embodiments of hypodermic needles, or variations thereof herein described, may be packaged and/or sold in such a combination with a syringe as a single unit.

While several embodiments and modifications thereto of the invention have been shown and described herein as best modes for carrying out the invention, it should be understood that changes and modifications may be made thereto without departing from the subject matter coming within the scope of the invention and the following claims.

I claim:

1. A safety hypodermic needle comprising:
    a) a needle provided with a passageway there through for the transmission of fluids, said needle being sharpened at its distal end to form a piercing end;
    b) a hub connected with the proximal end of said needle, said hub being engagable with a syringe so that fluid may be transmitted between said syringe and said needle, passing through said needle;
    c) a hollow member including a hole or a groove therein, said hollow member being positioned over a portion of said needle so that said needle passes into or through said hole or said groove;
    d) a spring positioned between said hollow member and said hub;
    e) at least one supporting member connected with said hollow member, said supporting member including a rearward extending portion adapted to engage said hub;
    f) a releasable securement means for holding said hollow member away from the piercing end of said needle, against tension from said spring, so that after said hollow member is released by said securement means, said hollow member will move forward along said needle, by force of said spring, and at least partially cover said piercing end of said needle, with support means being provided for said rearward extending portion of said supporting member to engage said hub to support said hollow member against movement back toward said hub that would reexpose said piercing end of said needle.

2. The safety hypodermic needle of claim 1, wherein two supporting members extend rearward from said hollow member.

3. The safety hypodermic needle of claim 1, wherein said one or more supporting members and said hollow member are plastic and are formed together as a single piece in a plastic injection mold without a slide.

4. The safety hypodermic needle of claim 1, wherein said releasable securement means is a bond formed by the melting and solidifying together of a small amount of plastic from said hub and said at least one supporting member of said safety hypodermic needle.

5. The safety hypodermic needle of claim 1, wherein said support means is provided by the end or ends of said one or more supporting members adapted to push against the frontal surface of said hub.

6. The safety hypodermic needle of claim 5, wherein said rearward extending portion of said one or more supporting members curve inward, toward the axial center of the hypodermic needle, as said one or more supporting members extend rearward away from said hollow member, when said hollow member is in the forward position at least partially covering said piercing end of said needle.

7. The safety hypodermic needle of claim 6, wherein said one or more supporting members and said hollow member are plastic and are formed together as a single piece in a plastic injection mold without a slide.

8. The safety hypodermic needle of claim 5, wherein said one or more supporting members and said hollow member are plastic and are formed together as a single piece in a plastic injection mold without a slide.

9. The safety hypodermic needle of claim 1, wherein said support means is provided by a stop or protrusion at or near the end of said one or more supporting members and positioned in a groove or depression in said hub.

10. The safety hypodermic needle of claim 9, wherein said one or more supporting members and said hollow member are plastic and are formed together as a single piece in a plastic injection mold without a slide.

11. A safety hypodermic needle comprising:
    a) a needle provided with a passageway there through for the transmission of fluids, said needle being sharpened at its distal end to form a piercing end;
    b) a hub connected with the proximal end of said needle, said hub being engagable with a syringe so that fluid may be transmitted between said syringe and said needle, passing through said needle;
    c) a hollow member including a hole or a groove therein, said hollow member being positioned over a portion of said needle so that said needle passes into or through said hole or said groove;
    d) at least one supporting member connected with said hollow member, said supporting member including a rearward extending portion adapted to engage said hub;
    e) a releasable securement means for holding said hollow member away from the piercing end of said needle, so that after said hollow member is released by said securement means, said hollow member may be moved forward, along said needle, to a position at least partially covering said piercing end of said needle, with support means provided for said rearward extending portion of said supporting member to engage said hub to support said hollow member against movement back toward said hub that would reexpose said piercing end of said needle.

12. The safety hypodermic needle of claim 11, wherein two supporting members extending rearward from said hollow member.

13. The safety hypodermic needle of claim 11, wherein said one or more supporting members and said hollow member are plastic and are formed together as a single piece in a plastic injection mold without a slide.

14. The safety hypodermic needle of claim 11, wherein said releasable securement means is a bond formed by the melting and solidifying together of a small amount of plastic from said hub and said at least one supporting member of said safety hypodermic needle.

15. The safety hypodermic needle of claim 11, wherein said support means is provided by a stop or protrusion at or near the end of said one or more supporting members and positioned in a groove or depression in said hub.

16. The safety hypodermic needle of claim 15, wherein said releasable securement means is a bond formed by the melting and solidifying together of a small amount of plastic from said hub and said at least one supporting member of said safety hypodermic needle.

17. The safety hypodermic needle of claim 15, wherein said one or more supporting members and said hollow member are plastic and are formed together as a single piece in a plastic injection mold without a slide.

18. In combination with a syringe, a safety hypodermic needle comprising:
 a) a needle provided with a passageway there through for the transmission of fluids, said needle being sharpened at its distal end to form a piercing end;
 b) a hub connected with the proximal end of said needle, said hub being engaged with said syringe so that fluid may be transmitted between said syringe and said needle, passing through said needle;
 c) a hollow member including a hole or a groove a therein, said hollow member being positioned over a portion of said needle so that said needle passes into or through said hole or said groove;
 d) a spring positioned between said hollow member and said hub;
 e) at least one supporting member connected with said hollow member, said supporting member including a rearward extending portion adapted to engage said hub;
 f) a releasable securement means for holding said hollow member away from the piercing end of said needle, against tension from said spring, so that after said hollow member is released by said securement means, said hollow member will move forward along said needle, by force of said spring, and at least partially cover said piercing end of said needle, with support means provided for said rearward extending portion of said supporting member to engage said hub to support said hollow member against movement back toward said hub that would reexpose said piercing end of said needle.

19. The combination of claim 18, wherein two supporting members extend rearward from said hollow member.

20. The combination of claim 18, wherein said one or more supporting members and said hollow member are plastic and are formed together as a single piece in a plastic injection mold without a slide.

21. The combination of claim 18, wherein said releasable securement means is a bond formed by the melting and solidifying together of a small amount of plastic from said hub and said at least one supporting member of said safety hypodermic needle.

22. The combination of claim 18, wherein said support means is provided by the end or ends of said one or more supporting members adapted to push against the frontal surface of said hub.

23. The combination of claim 22, wherein said one or more supporting members and said hollow member are plastic and are formed together as a single piece in a plastic injection mold without a slide.

24. The combination of claim 22, wherein said rearward extending portion of said one or more supporting members curve inward, toward the axial center of the hypodermic needle, as said one or more supporting members extend rearward away from said hollow member, when said hollow member is in the forward position at least partially covering said piercing end of said needle.

25. The combination of claim 24, wherein said one or more supporting members and said hollow member are plastic and are formed together as a single piece in a plastic injection mold without a slide.

26. The combination of claim 18, wherein said support means is provided by a stop or protrusion at or near the end of said one or more supporting members and positioned in a groove or depression in said hub.

27. The combination of claim 26, wherein said one or more supporting members and said hollow member are plastic and are formed together as a single piece in a plastic injection mold without a slide.

28. In combination with a syringe, a safety hypodermic needle comprising:
 a) a needle provided with a passageway there through for the transmission of fluids, said needle being sharpened at its distal end to form a piercing end;
 b) a hub connected with the proximal end of said needle, said hub being engaged with said syringe so that fluid may be transmitted between said syringe and said needle, passing through said needle;
 c) a hollow member including a hole or a groove therein, said hollow member being positioned over a portion of said needle so that said needle passes into or through said hole or said groove;
 d) at least one supporting member connected with said hollow member, said supporting member including a rearward extending portion adapted to engage said hub;
 e) a releasable securement means for holding said hollow member away from the piercing end of said needle, so that after said hollow member is released by said securement means, said hollow member may be moved forward, along said needle, to a position at least partially covering said piercing end of said needle, with support means provided for said rearward extending portion of said supporting member to engage said hub to support said hollow member against movement back toward said hub that would reexpose said piercing end of said needle.

29. The combination of claim 28, wherein two supporting members extend rearward from said hollow member.

30. The combination of claim 28, wherein said one or more supporting members and said hollow member are plastic and are formed together as a single piece in a plastic injection mold without a slide.

31. The combination of claim 28, wherein said releasable securement means is a bond formed by the melting and solidifying together of a small amount of plastic from said hub and said at least one supporting member of said safety hypodermic needle.

32. The combination of claim 28, wherein said support means is provided by a stop protrusion at or near the end of said one or more supporting members and positioned in a groove or depression in said hub.

33. The combination of claim 32, wherein said releasable securement means is a bond formed by the melting and solidifying together of a small amount of plastic from said hub and said at least one supporting member of said safety hypodermic needle.

34. The combination of claim 32, wherein said one or more supporting members and said hollow member are plastic and are formed together as a single piece in a plastic injection mold without a slide.

* * * * *